United States Patent
Mannapur et al.

(10) Patent No.: US 10,241,022 B2
(45) Date of Patent: Mar. 26, 2019

(54) CHARACTERIZING A FLUID SAMPLE BASED ON RESPONSE OF A NON-PLANAR STRUCTURE

(71) Applicant: Intel Corporation, Santa Clara, CA (US)

(72) Inventors: Vishal Mannapur, Folsom, CA (US); Handeep Kaur, Mather, CA (US); Yuri I. Krimon, Folsom, CA (US); David I. Poisner, Carmichael, CA (US); Anand K. Enamandram, Folsom, CA (US)

(73) Assignee: Intel Corporation, Santa Clara, CA (US)

( * ) Notice: Subject to any disclaimer, the term of this patent is extended or adjusted under 35 U.S.C. 154(b) by 140 days.

(21) Appl. No.: 15/474,530

(22) Filed: Mar. 30, 2017

(65) Prior Publication Data

US 2018/0284006 A1    Oct. 4, 2018

(51) Int. Cl.
*G01N 15/08* (2006.01)

(52) U.S. Cl.
CPC ....... *G01N 15/08* (2013.01); *G01N 2015/086* (2013.01)

(58) Field of Classification Search
CPC ..................................................... G01N 15/08
See application file for complete search history.

(56) References Cited

U.S. PATENT DOCUMENTS

| 5,082,626 A | * | 1/1992 | Grage, Jr. | ............. | B01L 3/5027 |
| | | | | | 422/408 |
| 6,327,410 B1 | * | 12/2001 | Walt | ..................... | B01J 19/0046 |
| | | | | | 359/900 |
| 7,105,354 B1 | | 9/2006 | Shimoide et al. | | |
| 2003/0064507 A1 | * | 4/2003 | Gallagher | ................. | B01F 9/10 |
| | | | | | 435/287.2 |
| 2004/0137465 A1 | * | 7/2004 | Kain | ..................... | B01J 19/0046 |
| | | | | | 435/6.11 |
| 2005/0266074 A1 | | 12/2005 | Zilberstein et al. | | |
| 2010/0272608 A1 | * | 10/2010 | Penterman | ............. | G01K 11/00 |
| | | | | | 422/69 |

(Continued)

FOREIGN PATENT DOCUMENTS

KR    20030047970 A    6/2003

OTHER PUBLICATIONS

Wu, J., "Biased AC Electro-Osmosis for On-Chip Bioparticle Processing," IEEE Transactions on Nanotechnology, vol. 5, No. 2, Mar. 2006, pp. 84-89.

(Continued)

*Primary Examiner* — David A Rogers
(74) *Attorney, Agent, or Firm* — Schwabe, Williamson & Wyatt, P.C.

(57) ABSTRACT

Apparatuses, methods and storage medium associated with characterizing a fluid sample based on response of a non-planar structure are disclosed herein. In embodiments, an apparatus may include a non-planar structure having an exterior (e.g., a curved exterior) and a core having a content to change (e.g., by osmosis) responsive to application of the fluid sample to the non-planar structure. The apparatus may include one or more processors, devices, and/or circuitry to identify a value indicative of a characteristic of the fluid based on the measurement. Other embodiments may be disclosed or claimed.

25 Claims, 5 Drawing Sheets

(56) References Cited

U.S. PATENT DOCUMENTS

| | | | |
|---|---|---|---|
| 2010/0310423 A1* | 12/2010 | Nieuwenhuis | B01L 3/5027 422/82.05 |
| 2014/0134602 A1* | 5/2014 | Van Zon | G01N 21/552 435/5 |
| 2015/0001071 A1* | 1/2015 | Le Neel | G01N 27/327 204/403.04 |
| 2015/0196254 A1* | 7/2015 | Park | A61B 5/702 600/365 |

OTHER PUBLICATIONS

Prakash, S, et al., "Theory, Fabrication and Applications of Microfluidic and Nanofluidic Biosensors," Phil. Trans. R. Soc. A 370, 2269-2303 doi:10.1098/rsta.2011.0498, retrieved from URL <<http://rsta.royalsocietypublishing.org/.. Downloaded from http://rsta.royalsocietypublishing.org/ on Oct. 22, 2016.

* cited by examiner

CHARACTERIZING A FLUID SAMPLE BASED ON RESPONSE OF A NON-PLANAR STRUCTURE

TECHNICAL FIELD

The present disclosure relates to fluid sample testing and more specifically relates to characterizing a fluid sample based on response (e.g., by osmosis) of a non-planar structure.

BACKGROUND

The background description provided herein is for the purpose of generally presenting the context of the disclosure. Unless otherwise indicated herein, the materials described in this section are not prior art to the claims in this application and are not admitted to be prior art by inclusion in this section.

Devices for chemical analysis may include a film formed on a semiconductor substrate. The film may provide an indication of a concentration of a substance in a fluid, e.g., a liquid or a gas. For instance, in blood glucose monitoring, a drop of blood may be placed on a disposable strip which interfaces with a digital blood glucose meter. A blood glucose level may be shown on a display of the digital blood glucose meter. To decrease costs, increase accuracy, increase speed, expand the scope of materials that may be measured, and/or for other reasons, alternatives to chemical analysis using films formed on a semiconductor substrate are needed.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

DETAILED DESCRIPTION

Figure 1:
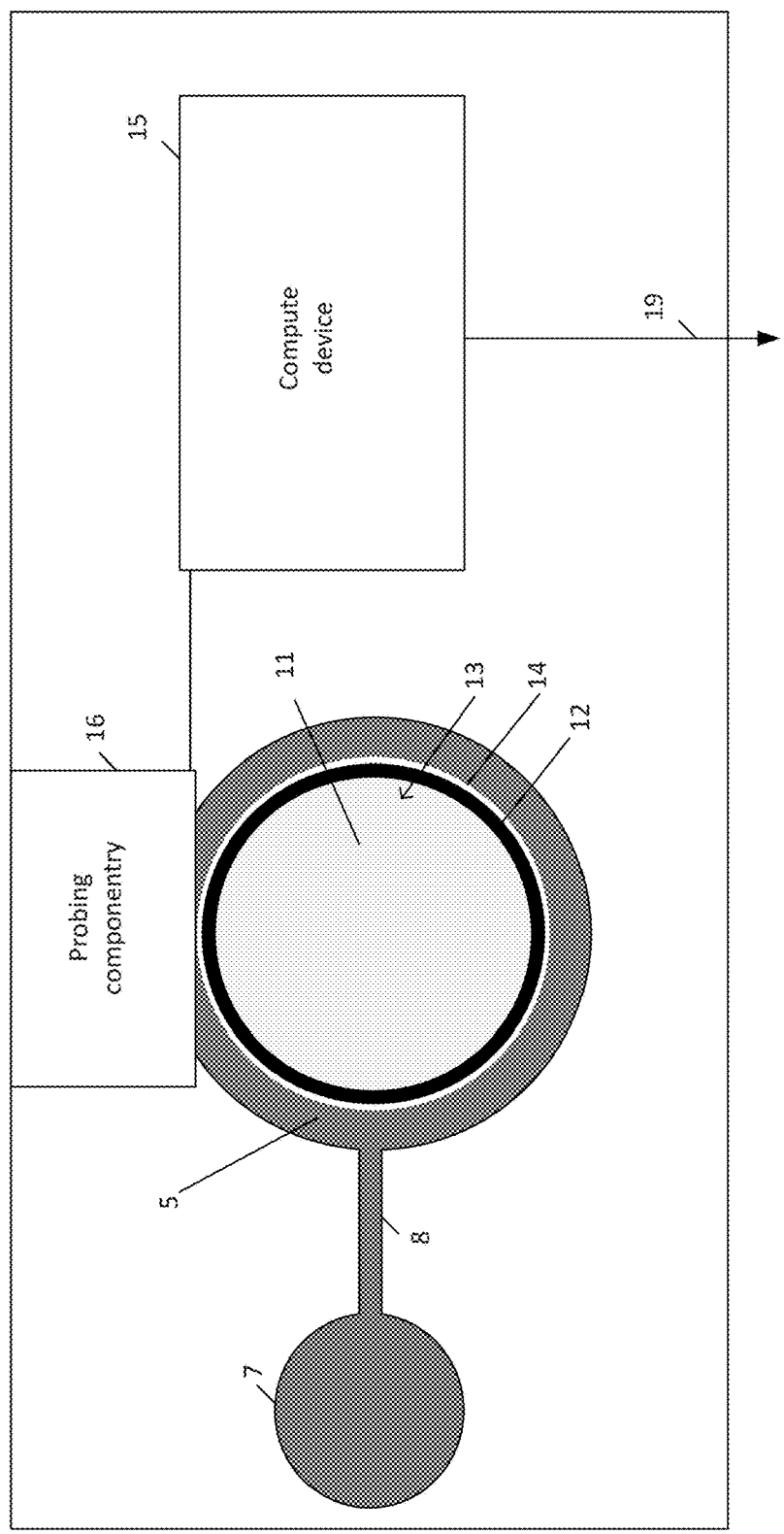
FIG. 1 illustrates an example system equipped with technology for characterizing a fluid sample based on response of a non-planar structure, according to various embodiments.

Apparatuses, methods and storage medium associated with characterizing a fluid sample based on response (e.g., by osmosis) of a non-planar structure are disclosed herein. In embodiments, an apparatus may include a non-planar structure having an exterior (e.g., a curved exterior) and a core having a content to change (e.g., by osmosis) responsive to application of the fluid sample to the non-planar structure. The apparatus may include one or more processors, devices, and/or circuitry to identify a value indicative of a characteristic of the fluid based on the measurement.

In the following detailed description, reference is made to the accompanying drawings which form a part hereof wherein like numerals designate like parts throughout, and in which is shown by way of illustration embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that like elements disclosed below are indicated by like reference numbers in the drawings.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

As used herein, the term "circuitry" may refer to, be part of, or include an Application Specific Integrated Circuit (ASIC), an electronic circuit, a processor (shared, dedicated, or group) and/or memory (shared, dedicated, or group) that execute one or more software or firmware programs, a combinational logic circuit, and/or other suitable components that provide the described functionality.

Lab-on-a-Chip (LOC) is a microtechnology for performing one or more measurement processes that may have been done in a lab in legacy processes and shrinks them down into a chip, e.g., a single chip. Advantages of LOC may include significantly lower cost, reduced time to get results, and reduced need for specialized labor.

Some embodiments disclosed herein include apparatus and/or methods to measure various changes in a fluid environment. Some embodiments utilize a three dimensional structure, e.g., a non-planar structure, such as a bead. These beads are small absorbent structures that are able to change their properties based on absorption or perspiration of molecules. These beads may come in a variety of shapes, sizes, internal composition, and coatings, and may grow or shrink in size based on osmosis. Examples of beads may include super absorbent polymer (SAP) structures, poly acrylamide structures, hydrated water gel structures, water beads, or the like.

Some beads may include a selective semipermeable membrane (to suggest of this selective quality of the bead and/or the processes for identifying a characteristic of a fluid sample using the bead, the bead may be referred to as a "smartbead"). Smartbeads may include one or more of the attributes that follow below.

- May include an organic polymer material that may respond to osmolality changes by expanding or contracting volumetrically.
- Selected substance (e.g., selected molecules such as $H_2O$) may be able to pass by diffusion, facilitated diffusion, passive or active transport, or the like, or combinations thereof.
- The rate of expansion may be controlled based on the composition of the bead.
- The rate of expansion may be determined by the water/electrolyte content of the liquid.
- The beads may slowly release water/ions back into their environment through osmosis.
- Osmosis may allow only a selected material to diffuse through (e.g., water with no salt or other contaminants).
- May utilize reverse osmosis to pass selective compounds, like electrolytes ($Na+$, $Cl-$, $K+$, $HCO_{3\_}$).
- May be beads of various shapes and sizes. It is not necessary for beads to be in a perfect sphere or even a sphere. Different beads can be "tuned" to different absorptions to characterize a given fluid sample (e.g., could characterize a fluid sample using, say, sixteen different beads with different absorption and/or expansion properties).
- A bead may be composed of stable polymer material to retain its shape when swelling or contracting.
- The inherent properties of the beads may be modulated to make them sensitive to different compounds or ratios of compounds using: material on the inside, material on the shell, surface coating on the shell, or the like, or combinations thereof.
- Electrical components may be embedded in the bead or connected to the surface of the bead. These electrical components may include sensors, conductive coating, or the like, or combinations thereof.

There may not be a limit to the size of beads; however, some beads may have a dimension (e.g., diameter, length, width, height, etc.) of one millimeter or smaller (in some examples). However, beads may be larger too and this wide range of sizes may allow scalability. Testing may be performed using various sample volume sizes and one or more beads of the same or different selectivity.

Properties of a bead may change as the bead is exposed to a fluid sample. Some embodiments disclosed herein use processes to detect a change in one or more of the properties of the beads, such as size, surface tension, viscosity, density, conductivity, capacitance, spectral patterns (light absorption, light transmission, optical transparency, etc.) or the like, or combinations thereof. Some embodiments may measure the change in the properties exposed to fluids, such as bodily fluids (blood, saliva, urine, etc.), water samples, beverages, cleaning fluids, solvents, or the like, or combinations thereof.

One example of a changing property is volumetric change. As the bead absorbs fluid, it may grow, where the growth may be dependent on the composition of the fluid (e.g., percentage of $H_2O$). Some embodiments may use one or more of the systems that follow below.

In one system, a bead may be positioned a predetermined distance from probing componentry including a small plate (e.g., micro-electro-mechanical system (MEMs) based) so that a side of the bead may push on the plate during growth, which may result in a change in an electrical characteristic (e.g., capacitance) that can be measured using a circuit of the probing componentry (based on distance between the plates between plates of the capacitor). In other examples, the movement of the plate may change a different electrical characteristic of a circuit (such as whether the circuit is open or closed), which can be measured by the probing componentry (e.g., determining whether the circuit is open or closed). A processor may calculate a value indicative of the composition of the fluid based on the measurement.

In another system, a bead may be positioned a predetermined distance from a plate (e.g., MEMs based) that is positioned in the path of a small laser and detector of the probing componentry. As the plate moves further in the beam path during growth, the reduction in the amount of light received at the detector may be measured. In other examples, the plate may be a hinged plate, the beam may be directed to the hinged plate, and the sensor may detect a change in an angle of reflection of the beam of light based on movement of the hinged plate. A processor may calculate a value indicative of the composition of the fluid based on the measurement.

In yet another system, a spherical bead (which may or may not be a perfect sphere) may be formed or deposited in a depression on a circuit board that includes probing componentry. A bottom of the depression may be hemisphere shaped (which may or may not be a perfect hemisphere, and may be to correspond with a shape of the bead). As the bead grows, the bead may lift slightly out of the depression. A resulting gap may increase a dielectric gap of a capacitor of the probing componentry of the circuit board. A circuit of the probing componentry may be used to measure a change in the capacitance based on growth. A processor may calculate a value indicative of the composition of the fluid based on the measured capacitance change.

In yet another system, a bead may be positioned inside a small conductive coil of probing componentry of a circuit board. As the bead grows it may push the coil apart resulting in a change in inductance that can be measured using a circuit of the probing componentry. A processor may calculate a value indicative of the composition of the fluid based on the measured inductance change.

In yet another system, a bead may be positioned on a Cartesian grid electrically coupled to a circuit of probing componentry or on a ring of concentric circles electrically coupled to the circuit. As the bead grows, it may come in contact with more of the grid lines or circles. For instance, a conductive coating on a portion of an exterior of the bead (e.g., a thin layer of graphite on an entire exterior surface of the bead) may come in contact with one or more of the grid lines. The circuit of the probing componentry may be used to detect the contact. A processor may calculate a value indicative of the composition of the fluid based on the detected change in contact.

Another example of a changing property is surface tension and/or viscosity. The surface tension and/or viscosity of a bead may change as the bead grows and as possible chemical reactions occur with coatings on the bead. Some embodiments may use one or more of the systems that follow below.

In one system, a bead is positioned proximate to probing componentry to apply targeted pressure on the bead (e.g., poke the bead). The pressure required to penetrate or achieve a predetermined deformation of the bead may be measured by the probing componentry. A processor may calculate a value indicative of the composition of the fluid based on the pressure measurement.

In another system, a bead is positioned proximate to probing componentry to measure deformation of the bead responsive to the bead being poked by a poker of the probing componentry. A processor may calculate a value indicative of the composition of the fluid based on the measured deformation.

In yet another system, a bead is positioned proximate to probing componentry to determine an ability of the bead to push against another object (e.g. ratio of top/side) or the probing componentry. A processor may calculate a value indicative of the composition of the fluid based on the measurement of the force (e.g., the pushing ability).

In yet another system, a bead may be positioned on a predetermined surface of probing componentry so that the bead can slide on the predetermined surface. A sensor of the probing componentry may measure a movement of a bead, which can be used to calculate a frictional coefficient. A processor may calculate a value indicative of the composition of the fluid based on the measurement of movement and/or the calculated frictional coefficient.

Another example of a changing property is vibrational response. Density and/or surface tension of the bead may change as the bead grows and/or possible chemical reactions occur with coating(s) on the bead. These changes may cause the bead to exhibit a different vibrational response to a predetermined vibration. Some embodiments may use one or more of the systems that follow below.

In one system, a bead may be positioned proximate to probing componentry including a vibration injector (such as a MEMs actuator) to impart a predetermined vibration at one point of the exterior of the bead (e.g., at a zenith of the exterior), and a sensor of the probing componentry may be used to measure vibration of a different point of the exterior (e.g., a nadir of the exterior). In some examples, the sensor may be an accelerometer, such as a laser deflection accelerometer. A processor may calculate a value indicative of the composition of the fluid based on the measurement.

In another system, a bead may be positioned proximate to probing componentry to impart a predetermined vibration at one point of the bead. A sensor of the probing componentry may be used to detect failure, such as bursting of the bead. A processor may calculate a value indicative of the composition of the fluid based on a binary indication of failure or not.

Another example of a changing property is electrical characteristics. As a bead absorbs fluid and/or ions (and possible chemical reaction with the contents of the bead occur), there may be changes to electrical characteristics such as impedance, capacitance, or the like, or combinations thereof.

In one system, a bead may be positioned proximate to probing componentry including an electrical probe coupled to one portion of the bead (e.g., the zenith), and another electrical probe of the probing componentry may couple to another portion of the bead (e.g., the nadir). A circuit of the probing componentry may be connected to the electrical probes and may identify impedance between the probes. A processor may calculate a value indicative of the composition of the fluid based on the impedance.

In another system, the bead may be positioned proximate to probing componentry including an electrical probe electrically coupled to one portion of the bead (e.g., the zenith), and another electrical probe of the probing componentry may be coupled to another portion of the bead (e.g., the nadir). A circuit of the probing componentry (connected to the electrical probes) may identify capacitance between the probes. A processor may calculate a value indicative of the composition of the fluid based on the capacitance.

Another example of a changing property is light absorption. As a bead absorbs fluid and/or ions (and possible chemical reaction with the contents of the bead occur), there may be changes to the way light is absorbed by the bead.

In one system, a bead may be positioned proximate to probing componentry including a light source and a photo detector placed at different sides of the bead (e.g., opposite sides). A processor may calculate a value indicative of the composition of the fluid based on a measurement of the photo detector.

Another example of a changing property is fluorescing. As a bead absorbs fluid and/or ions (and possible chemical reaction with the contents of the bead occur), there may be a fluorescing effect.

In one system, the bead may be illuminated by a UV (ultra violet) light source. The bead may be positioned proximate to probing componentry to measure the resulting spectrum. A processor may calculate a value indicative of the composition of the fluid based on the spectral measurement.

Another example of a changing property is direct mass measurement. As a bead absorbs fluid, a mass of the bead will increase.

In one system, the bead may be positioned proximate to probing componentry to measure the mass. A processor may calculate a value indicative of the composition of the fluid based on the mass measurement.

Another example of a changing property is percentage of fluid or amount of fluid absorbed.

In one system, a bead may be positioned proximate to probing componentry including a fluid reservoir. The bead may be in the fluid reservoir or a micro fluid channel may extend from the fluid reservoir to the bead (the fluid reservoir may be filled or fillable with a liquid or a gas that is denser than a gas of a testing environment so that the gas may travel along the channel). The probing componentry may measure a percentage and/or an amount of the liquid remaining in the reservoir (e.g., after fluid travels from the reservoir to the bead and/or from the bead to the reservoir). A processor may determine an amount of fluid absorbed and/or released using the measured percentage and/or amount, and calculate a value indicative of the composition of the fluid based on the determination.

Another example of a changing property is a surface area of the bead.

In one system, a bead may be positioned proximate to probing componentry including a sensing pad, e.g., the bead may rest on the sensing pad (with a portion of a bottom of the bead making physical contact with the sensing pad). The sensing pad may measure more contact as the bead expands and/or changes shape and a different portion of the bottom of the bead makes physical contact with the sensing pad. A processor may calculate a value indicative of the composition of the fluid based on the sensor pad measurement.

A system to identify a characteristic of a fluid sample may measure changes to more than one characteristic of a bead. Such a system may include a single bead with different types of probing componentry (e.g., more than one type of sensor and/or more than one type of actuator) to measure different characteristics of the bead. A processor may calculate a value indicative of the composition of the fluid based on the measurements.

A system may include more than one bead exposed to a same fluid sample (say a single reservoir). A first bead may be positioned proximate to a first portion of probing componentry to measure a first characteristic of the first bead, and a second bead may be positioned proximate to second portion of probing componentry to measure a second characteristic of the second bead. The measured characteristics may be the same or different. A processor may calculate a value indicative of the composition of the fluid based on the measurements.

In embodiments using more than one bead, the beads may be non-uniform. Beads may have different size, shapes, coatings, or the like, or combinations thereof. Different beads may be selective to different compounds. A processor may calculate a plurality of values indicative of the composition of the fluid based on the measurements. Each value may correspond to a different one of the compounds and/or a different property of the fluid sample.

Some embodiments may include one or more additional beads for self-calibration of a system. The system may include a reservoir for a known liquid and a reservoir for an unknown liquid. One bead may be exposed to the known liquid and another bead may be exposed to the unknown liquid. A processor may calculate a value indicative of the composition of the unknown fluid and a value indicative of the composition of the known fluid based on measurements of probing componentry. The processor may output or store a binary value indicating whether or not the test was successful based on a comparison of the value for the known fluid to an expected value of the known fluid. Use of additional beads for self-calibration of a system may be used to isolate changes due to temperature or aging of materials, such as the beads, the fluid sample, the probing componentry, etc.

FIG. 1 illustrates an example system equipped with technology for characterizing a fluid sample based on response of a non-planar structure, according to various embodiments. The system 100 may include a non-planar structure 13, which is depicted by a top cross-sectional view. The non-planar structure 13 may include a core 11 and an exterior 12. The exterior 12 may include a semi-permeable membrane to permeate a fluid sample 5 to or from the core 11, and a coating 14 may be formed on a portion of the membrane. In some embodiments, the fluid sample 5 may be a fluid to move to or from a reservoir 7 via a channel 8 (e.g., a micro fluid channel). The drawing is not necessarily to scale for at least some embodiments—in some embodiments the reservoir 7 may be larger than the non-planar structure 13, which may be a bead having a dimension (e.g., diameter, length, width, height, etc.) of one millimeter or smaller (in some examples). The non-planar structure 13 may be similar to any non-planar structure described herein.

A shape of the non-planar structure 13 may be three dimensional, such as a sphere, a spheroid, a truncated sphere (such as a hemisphere), or a truncated sphere (in at least one of its states, such as a saturated state) in some embodiments. The non-planar structure 13 may have different shapes in different states such as saturated state (e.g., filled), non-saturated state, and in some cases a ruptured state.

The system 100 may include a compute device 15 to calculate a value 19 indicative of a property of the fluid sample 5. The value 19 may be output over a user interface, such as a display (not shown, may be remote or local). The compute device 15 may identify the change in the characteristic of the non-planar structure 13 using probing componentry 16. The compute device 15 may include a communication component (not shown) to transmit the value 19 via WiFi®, Bluetooth®, Universal Serial Bus® (USB), or the like, or combinations thereof, to a user terminal for outputting over a user interface and/or to backend services (not shown) for further processing/reporting/storage/etc. The compute device 15 may be similar to any compute device (e.g., processor) described herein.

The non-planar structure 13 may be positioned proximate to probing componentry 16. The probing componentry 16 may be similar to any probing componentry described herein. The probing componentry 16 may be to measure different characteristics of a same non-planar structure 13, and may include a number of sensors and/or a number of actuators. In some embodiments, the probing componentry 16 may include one or more sensors and no actuators, such as in a direct mass measurement. In other examples, the probing componentry 16 may include one or more actuators to obtain the measurement using the sensor, such as an actuator to apply current to the non-planar structure 13, an actuator to project light on the non-planar structure 13, an actuator to apply mechanical stress on the non-planar structure 13, an actuator to apply an air pressure change to the non-planar structure 13, or the like, or combinations thereof. The probing componentry 16 may include more than one of the same type of sensor and/or actuator to obtain the measurement of the non-planar structure 13 and an additional non-planar structure (not shown), which may be the same or different as the non-planar structure 13 and may be exposed to the same or different reservoir 7.

Figure 2:
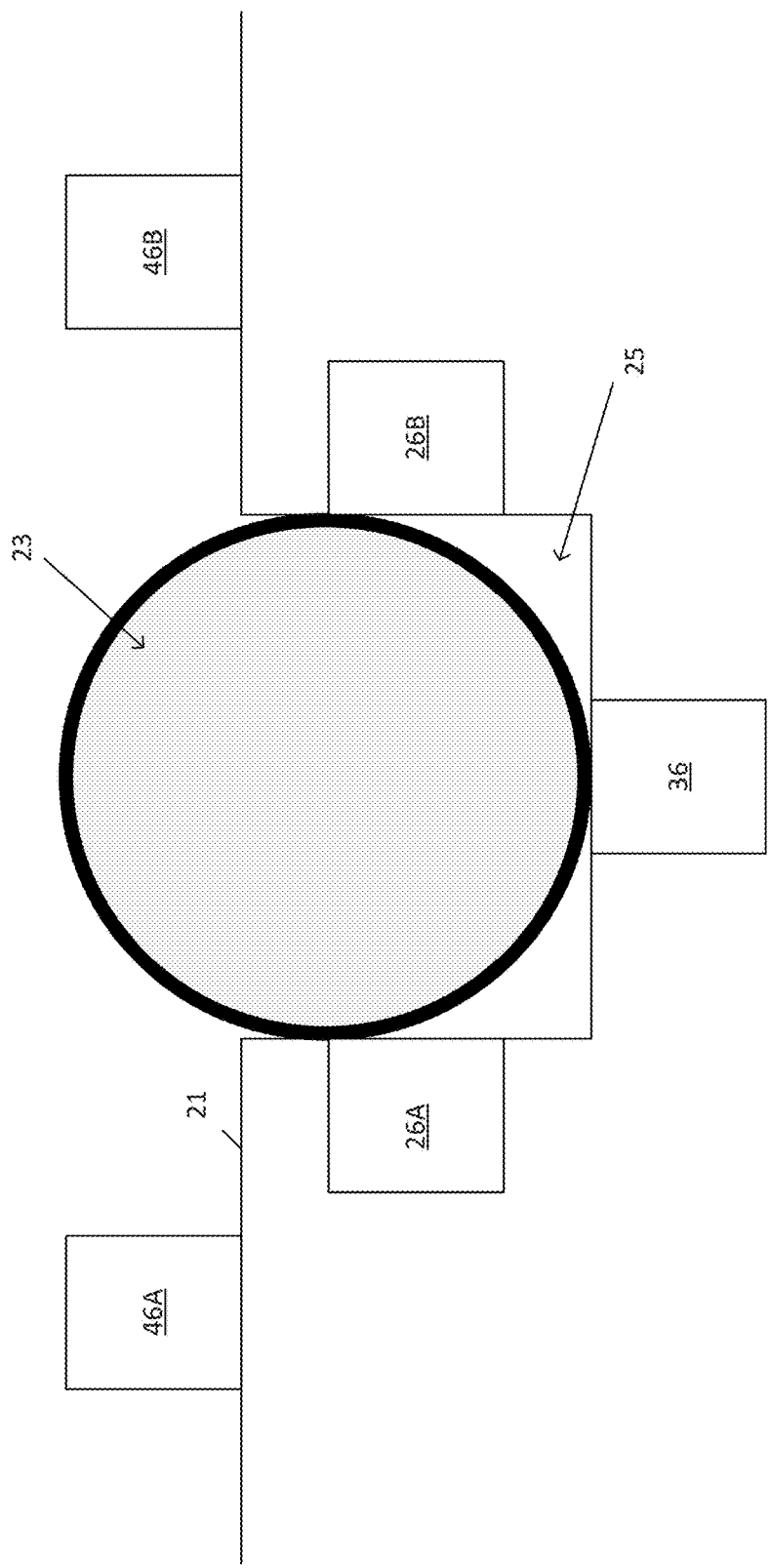
FIG. 2 illustrates a cross-sectional view of another example system equipped with technology for characterizing a fluid sample based on response of a non-planar structure, according to various embodiments.

FIG. 2 illustrates a cross-sectional view of another example system 200 equipped with technology for characterizing a fluid sample based on response of a non-planar structure, according to various embodiments. The system 200 may include a non-planar structure 23 formed in an opening 25 on a substrate 21. Non-planar structure may be similar to any non-planar structure described herein. The substrate 21 may be a semiconductor substrate or a printed circuit board. The opening 25 may be formed by etching or any other process to remove material. The opening 25 may have vertical sidewalls (as illustrated), but in other embodiments the opening 25 may have non-vertical sidewalls (such as sloping sidewalls and/or sidewalls to form a depression shaped to correspond with a shape of the non-planar structure 23, such as hemispherical in the case of a spherical shaped bead).

In some embodiments, the non-planar structure 23 may protrude from the opening 25 such that a top of the non-planar structure 13 (e.g., the zenith in the case of a spherical shape non-planar structure 23) in one or more states, as illustrated. In other embodiments, the non-planar structure 23 may not protrude from the opening 25 in any state.

In some embodiments, probing componentry may be formed in sidewalls of the opening 25, at a bottom of the opening 25, and/or on the surface of the substrate 21. The probing componentry may include components 26A-B, 36, and/or 46A-B, and may be similar to any of the probing componentry described herein.

Components 26A-B may include conductive structures to form a capacitor across the opening 25. A circuit coupled to the conductive structures may measure capacitance. Capacitance may change based on a change in the size of the non-planar structure 23 and/or a change of contents of a core of the non-planar structure 23. In some embodiments, component 36 may be a capacitor plate. A conductive layer (not shown) may be formed over the surface of the substrate 21 above the opening 25, and capacitance may change between component 36 and the conductive layer.

One of components 46A-B may be a light source and the other of components 46A-B may be a photo sensor. In cases where the light sensor and photo sensor are located on opposite sides of the opening 25, measurement may be based on a size of a shadow cast on the senor by the non-transparent non-planar structure 23. However, in other embodiments the components 46A-B may be oriented differently to reflect a beam of light off the non-planar structure 23 into the photo sensor to measure changes in reflective characteristics of the non-planar structure 23. In yet another embodiment, the light sensor and photo sensor may be located on opposite sides to determine a transparency of the non-planar structure 23. Any light sources described herein may output visible light, UV light, infrared light, or the like, or combinations thereof. In some embodiments, the photo sensor may be one or more one pixel cameras.

In other embodiments, one of components 46A-B may be a piezo electric actuator, and the other of components 46A-B may include optical components (light source and sensor) to identify a light scatter by the non-planar structure 23 to measure vibrational response (indicative of surface tension and/or viscosity). In other embodiments, the other of components 46A-B may be a non-optical sensor to detect a transient response change of the non-planar structure 23 responsive to injecting vibration with the piezo electric or MEMS actuator.

An actuator of the components 46A-B may output a signal that is the same for a given duration. However, in some examples the signal may change over a given duration. For instance, to measure changes in surface tension a signal may start at 1 Hz and sweep up to 100 KHz. This may utilize a single actuator or a plurality of actuators to activate sequentially to sweep the range. Similarly, a light source may be capable of different frequencies and/or more than one light source may be used to actuate using a range (for example infrared to a selected frequency of visible light).

In some embodiments, component 36 may be a vibration injector and the system 200 may include at least one of components 46A-B. The one of components 46A-B may be a laser deflection accelerator to measure transient vibration response after activation of component 36. In some embodiments, component 36 may be a light sensor and the bead 23 may be transparent in at least one state, and component 36 may determine whether ambient light passes through the bead 23 in one or more states. In some embodiments, component 36 may be a pressure sensor (e.g., MEMs based) to measure a mass of the bead 23 (e.g., the bead may weighed using a very small scale).

In some embodiments, at least one of components 36, 26A, 26B, 46A, or 46B may be a conductive grid coupled to one or more circuits. The bead 23 may have conductive coatings on a portion of its exterior. As the bead 23 changes size circuit(s) may be closed or opened and this can be measured to determine changes in size of the bead 23.

In some embodiments, a coating of the bead 23 may include a conductive trace printed on an exterior of the bead 23. The conductive trace may be spiral that goes around the bead 23. A change of length of the conductive trace can be measured by injecting a signal into one end of the trace and determining an amount of delay before the signal reaches the other end of the trace. The spiral may be formed on an exposed portion of the bead 23 that protrudes from the opening 25 (e.g., stamped on the exposed portion using conductive ink, printed using a printer with conductive ink, or the like, or combinations thereof). This spiral may start at a zenith of the bead 23 and spiral outwards, in some examples. In some examples, the conductive trace may make physical contact with at least one of components 36, 26A, 26B, 46A, or 46B in at least one state of the bead 23. Other electrical characteristics such as capacitance or inductance can be measured by a change in the length of the trace.

In another example, conductive layers on sidewalls or a bottom of the opening may form a conductive cage. A circuit may close as a conductive coating on a portion of the bead 23 contacts different locations of the cage.

Figure 3:
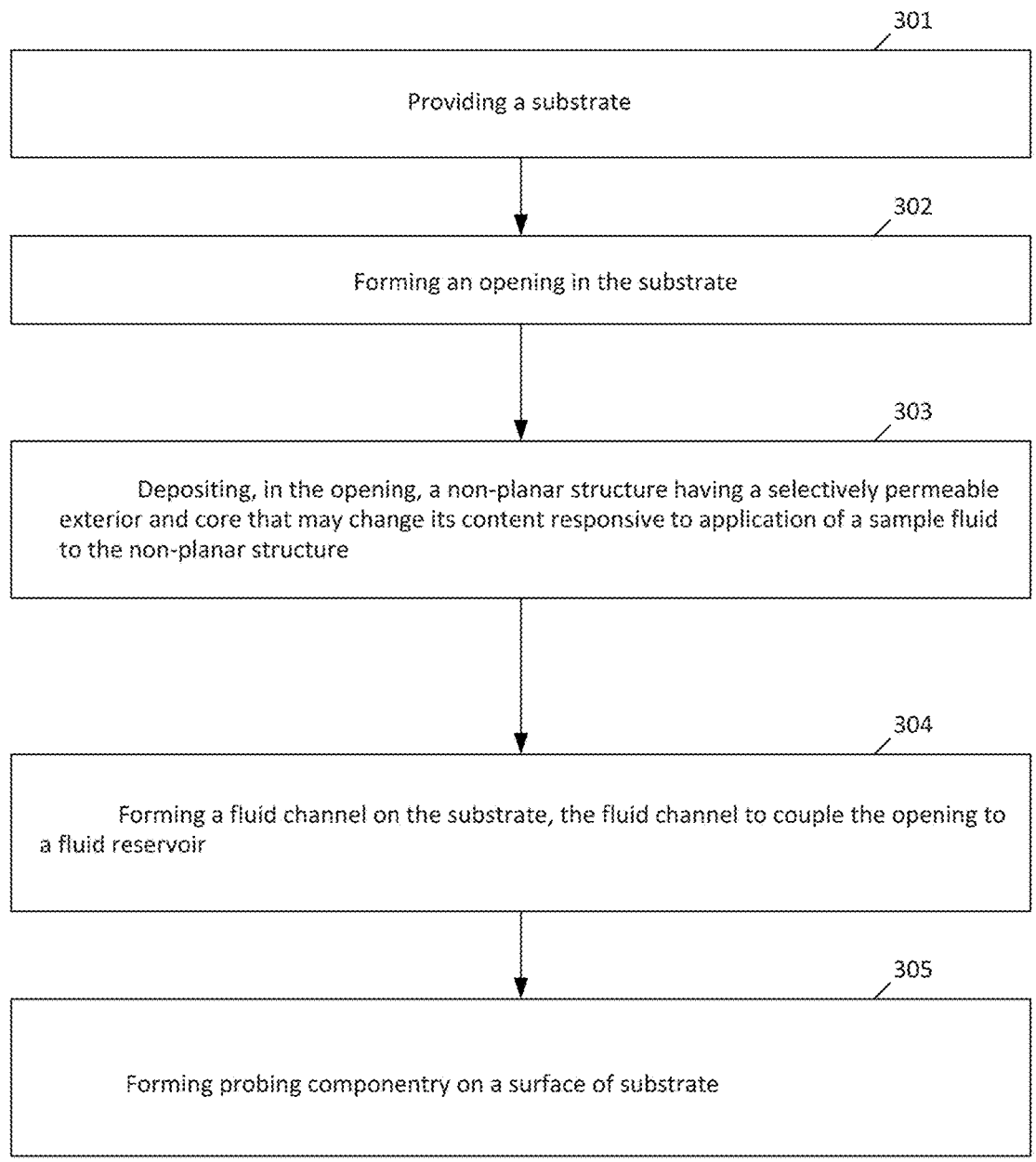
FIG. 3 is a flow chart showing a process of forming the system of FIG. 2.

FIG. 3 is a flow chart showing a process of forming the system of FIG. 2. In block 301 a substrate may be provided. The substrate may be a PCB. The substrate may be semiconductor substrate. The substrate may be formed from one or more layers that may include active circuitry. The active circuitry may include a processor to calculate a value indicative of a property of a fluid sample and/or one or more components (e.g., a circuit) of probing componentry to be proximate to a non-planar structure.

In block 302, an opening for the non-planar structure may be formed in the substrate. The opening may be formed by an etching process or any other process to remove material.

In block 303, the non-planar structure may be deposited in the opening. The non-planar structure may be similar to any non-planar structure described herein, and may have a selectively permeable exterior and core that may change its content (e.g., by osmosis) responsive to application of a fluid sample to the non-planar structure. The deposited non-planar structure may protrude from the opening or may fit entirely inside the opening.

In block 304, a fluid channel may be formed on the substrate 304. The fluid channel may couple the opening to a fluid reservoir.

In block 305, probing componentry may be formed on the surface of the substrate. In one embodiment, block 305 probing componentry may be formed, in part, by forming one or more layers on the substrate, over the opening, and/or on the non-planar structure. In some embodiments, the non-planar structure 23 may be enclosed between the substrate and the one or more layers. For instance, a layer formed over the opening may have a conductive region to form a capacitor with a conductive region of a bottom of the opening. In some embodiments, a portion of the one or more layers formed over the opening may include an opening to form a void defined by both of the openings.

Figure 4:
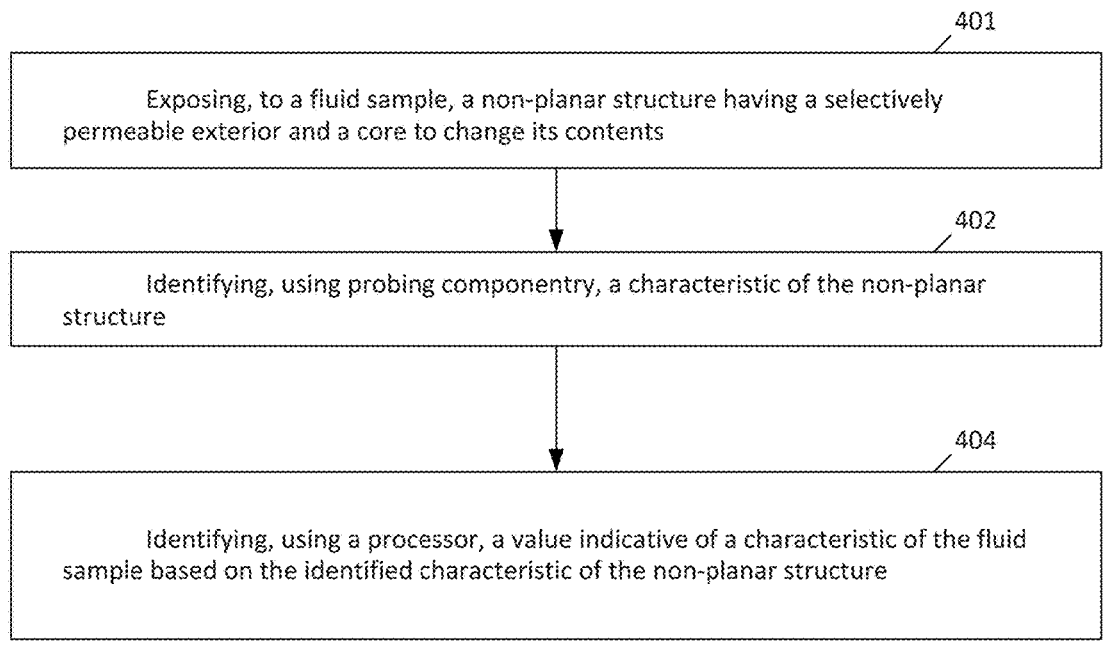
FIG. 4 is a flow chart showing a process of identifying a value indicative of a characteristic of a fluid sample using any of the systems described herein.

FIG. 4 is a flow chart showing a process of identifying a value indicative of a characteristic of a fluid sample using any of the systems described herein. In block 401, a non-planar structure may be exposed to a fluid sample. The non-planar structure may be similar to any non-planar structure described herein, and may include a selectively permeable exterior and a core to change its contents responsive to the exposure.

In block 402, probing componentry may be used to identify a characteristic of the non-planar structure. The probing componentry may be similar to any probing componentry described herein.

In block 403, a process may identify a value indicative of a characteristic of the fluid sample based on the identified characteristic of the non-planar structure. The processor may include more than one processor such as a first local processor to perform initial processing, and a second remote processor of backend services to receive a result of the initial processing by transmission from a communication interface and perform additional processing to identify the value.

Figure 5:
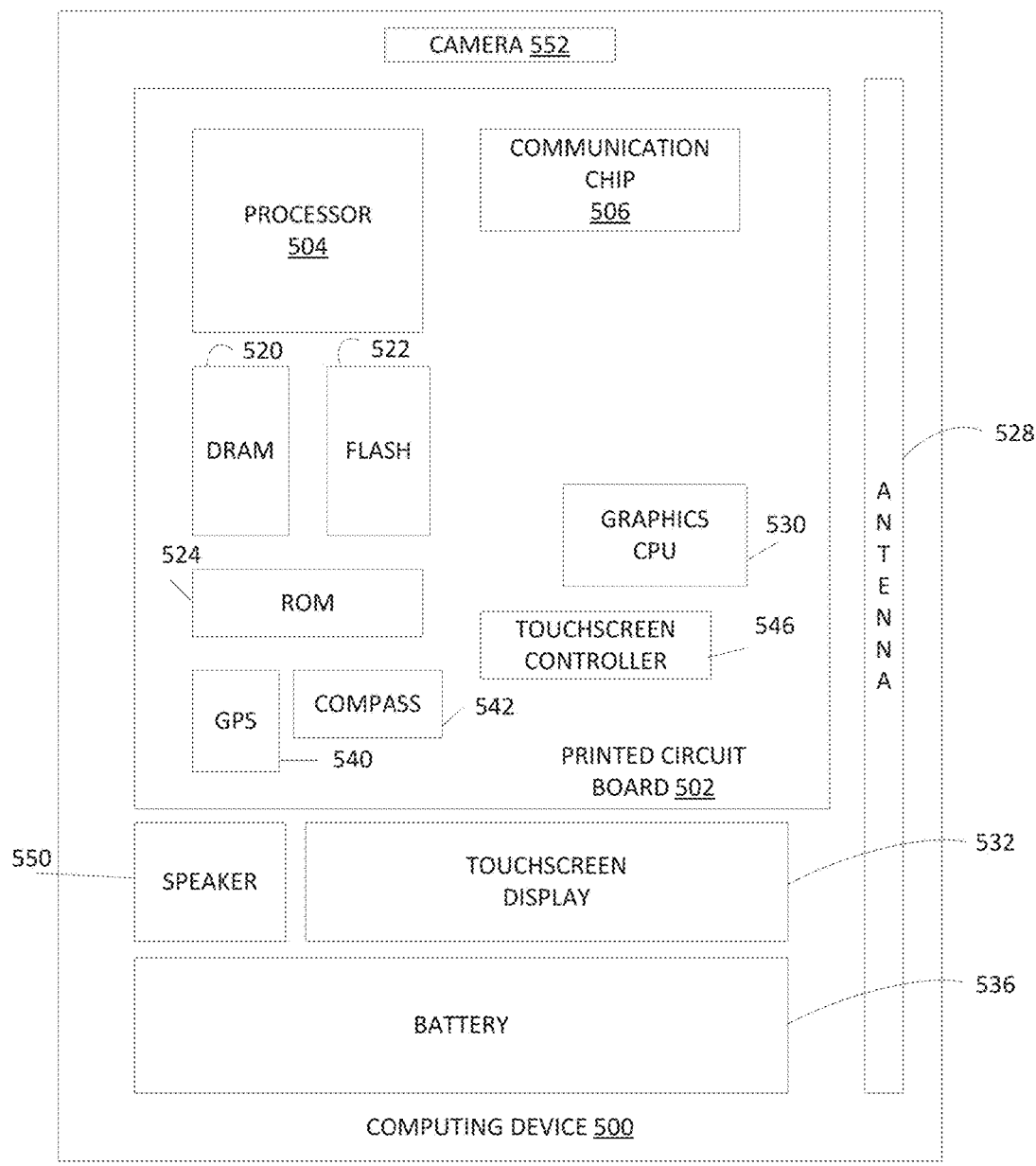
FIG. 5 illustrates an example computing device that may employ the apparatuses and/or methods described herein, according to various embodiments.

FIG. 5 illustrates an example device 500 that may employ the apparatuses and/or methods described herein, according to various embodiments (for instance, any apparatus and/or method associated with any compute device or electronic device described earlier with respect to FIGS. 1-4). As shown, device 500 may include a number of components, such as one or more processors 504 (one shown) and at least one communication chip 506. The communication chip 506 may have an interface to interface with probing componentry (not shown) to probe one or more non-planar structures (not shown). The one or more non-planar structures may be similar to any non-planar structures described herein, and the probing componentry may be similar to any probing componentry described herein.

In various embodiments, the one or more processors 504 each may include one or more processor cores. In various embodiments, the at least one communication chip 506 may be physically and electrically coupled to the one or more processors 504. In further implementations, the communication chip 506 may be part of the one or more processors 504. In various embodiments, computing device 500 may include printed circuit board (PCB) 502. For these embodiments, the one or more processors 504 and communication chip 506 may be disposed thereon.

In some embodiments, the one or more non-planar structures may be formed on the PCB 502, for instance, in one or more openings and/or predefined locations on the PCB 502. In these embodiments, one or more components of probing componentry may be formed on the PCB 502 proximate to the one or more non-planar structures (e.g., in and/or around the one or more openings). In some embodiments, the one or more non-planar structures and a portion of the probing componentry may be formed on a substrate (e.g., a substrate of PCB 502 or a different substrate) formed over one or more layers of active circuitry of the one or more processors 504 and/or the communication chip 506 (with conductive vias to send signals from the probing componentry to the one or more processors 504).

Depending on its applications, computing device 500 may include other components that may or may not be physically and electrically coupled to the PCB 502. These other components include, but are not limited to, a memory controller (not shown), volatile memory (e.g., dynamic random access memory (DRAM) 520), non-volatile memory such as read only memory (ROM) 524, flash memory 522, an I/O controller (not shown), a digital signal processor (not shown), a crypto processor (not shown), a graphics processor 530, one or more antenna 528, a display (not shown), a touch screen display 532, a touch screen controller 546, a battery 536, an audio codec (not shown), a video codec (not shown), a global positioning system (GPS) device 540, a compass 542, an accelerometer (not shown), a gyroscope (not shown), a speaker 550, a camera 552, and a mass storage device (such as hard disk drive, a solid state drive, compact disk (CD), digital versatile disk (DVD)) (not shown), and so forth.

In some embodiments, the one or more processor 504, flash memory 522, and/or a storage device (not shown) may include associated firmware (not shown) storing programming instructions configured to enable computing device 500, in response to execution of the programming instructions by one or more processor 504, to perform methods described herein such as processing data provided by the probing componentry and generating a value indicative of a characteristic of the fluid sample. In various embodiments, these aspects may additionally or alternatively be implemented using hardware separate from the one or more processor 504, flash memory 512, or storage device 511.

The communication chips 506 may enable wired and/or wireless communications for the transfer of data to and from the computing device 500. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. The communication chip 506 may implement any of a number of wireless standards or protocols, including but not limited to IEEE 702.20, Long Term Evolution (LTE), LTE Advanced (LTE-A), General Packet Radio Service (GPRS), Evolution Data Optimized (Ev-DO), Evolved High Speed Packet Access (HSPA+), Evolved High Speed Downlink Packet Access (HSDPA+), Evolved High Speed Uplink Packet Access (HSUPA+), Global System for Mobile Communications (GSM), Enhanced Data rates for GSM Evolution (EDGE), Code Division Multiple Access (CDMA), Time Division Multiple Access (TDMA), Digital Enhanced Cordless Telecommunications (DECT), Worldwide Interoperability for Microwave Access (WiMAX), Bluetooth, derivatives thereof, as well as any other wireless protocols that are designated as 3G, 5G, 5G, and beyond. The computing device 500 may include a plurality of communication chips 506. For instance, a first communication chip 506 may be dedicated to shorter range wireless communications such as Wi-Fi and Bluetooth, and a second communication chip 506 may be dedicated to longer range wireless communications such as GPS, EDGE, GPRS, CDMA, WiMAX, LTE, Ev-DO, and others.

In various implementations, the computing device 500 may be a wearable device, a laptop, a netbook, a notebook, an ultrabook, a smartphone, a computing tablet, a personal digital assistant (PDA), an ultra-mobile PC, a mobile phone, a desktop computer, a server, a printer, a scanner, a monitor, a set-top box, an entertainment control unit (e.g., a gaming console or automotive entertainment unit), a digital camera, an appliance, a portable music player, or a digital video recorder. In further implementations, the computing device 500 may be any other electronic device that processes data.

Any combination of one or more computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

EXAMPLES

Example 1 is an apparatus for characterizing a fluid sample based on response of a non-planar structure. The apparatus may include a substrate; a non-planar structure formed on the substrate, the non-planar structure having a semi-permeable membrane and a core defined by the semi-permeable membrane, the semi-permeable membrane to permeate a substance to or from the core, wherein a characteristic of the non-planar structure is to change responsive to the permeation of the substance through the semi-permeable membrane; and a sensor formed on the substrate, the sensor to obtain a measurement in response to exposure of the non-planar structure to a fluid sample; and circuitry to identify a value indicative of a characteristic of the fluid sample based on the measurement.

Example 2 includes the subject matter of example 1 (or any other example described herein), further comprising an actuator to perform at least one of apply current to the non-planar structure to obtain the measurement using the sensor, project light on the non-planar structure to obtain the measurement using the sensor, apply mechanical stress to an exterior surface of the semi-permeable membrane to obtain the measurement using the sensor, or apply an air pressure change to the exterior surface of the semi-permeable membrane to obtain the measurement using the sensor.

Example 3 includes the subject matter of any of examples 1-2 (or any other example described herein), wherein the actuator comprises at least one of a visible spectrum light source, a UV (ultra violet) spectrum light source, or an infrared spectrum light source.

Example 4 includes the subject matter of any of examples 1-3 (or any other example described herein), wherein the light comprises a laser beam.

Example 5 includes the subject matter of any of examples 1-4 (or any other example described herein), wherein the sensor is to measure a volume of a reservoir fluidly coupled to the non-planar structure responsive to the permeation of the fluid through the semi-permeable membrane.

Example 6 includes the subject matter of any of examples 1-5 (or any other example described herein), wherein the non-planar structure is formed in an opening on a surface of the substrate.

Example 7 includes the subject matter of any of examples 1-6 (or any other example described herein), wherein the semi-permeable membrane is to protrude from the surface.

Example 8 includes the subject matter of any of examples 1-7 (or any other example described herein), wherein the non-planar structure is formed entirely within an opening on a surface of the substrate.

Example 9 includes the subject matter of any of examples 1-8 (or any other example described herein), wherein the non-planar structure is to expand or contract responsive to absorption or perspiration of the fluid sample.

Example 10 includes the subject matter of any of examples 1-9 (or any other example described herein), wherein a shape of the non-planar structure comprises at least one of a sphere, a spheroid, a hemisphere, a truncated sphere, or a truncated spheroid.

Example 11 is an apparatus including a substrate; a non-planar structure formed on the substrate, the non-planar structure having a curved exterior and a core defined by the curved exterior, wherein a content of the core is to change by osmosis responsive to application of a fluid sample to the non-planar structure; and a module formed on the substrate to identify a change of a characteristic of the non-planar structure responsive to the application of the fluid sample to the non-planar structure, the identified change indicative of a property of the fluid sample.

Example 12 includes the subject matter of example 11 (or any other example described herein), wherein the module comprises a processor to: identify a measurement of a change in at least one of capacitance, resistance, or inductance responsive to a volumetric change of the non-planar structure; and calculate a value indicative of the property of the fluid sample based on the measurement.

Example 13 includes the subject matter of any of examples 11-12 (or any other example described herein), wherein the module comprises a processor to: identify a measurement of a change of position of a portion of the curved exterior responsive to a force applied to a different portion of the curved exterior; and calculate a value indicative of the property of the fluid sample based on the measurement.

Example 14 includes the subject matter of any of examples 11-13 (or any other example described herein), wherein the module comprises a processor to: identify a measurement of a change of vibrational response of the non-planar structure responsive to a force applied to the non-planar structure; and calculate a value indicative of the property of the fluid sample based on the measurement.

Example 15 includes the subject matter of any of examples 11-14 (or any other example described herein), wherein the module comprises a processor to: identify a measurement of a change in capacitance of a circuit that includes the non-planar structure; and calculate a value indicative of the property of the fluid sample based on the measurement.

Example 16 includes the subject matter of any of examples 11-15 (or any other example described herein), wherein the module comprises a processor to: identify a measurement of a change of an electrical characteristic of a circuit responsive to a change in conductivity of the non-planar structure; and calculate a value indicative of the property of the fluid sample based on the measurement.

Example 17 includes the subject matter of any of examples 11-16 (or any other example described herein), wherein the module comprises a processor to: identify a measurement of a change of at least one of optical transparency, optical reflection, or optical absorption of the non-planar structure; and calculate a value indicative of the property of the fluid sample based on the measurement.

Example 18 includes the subject matter of any of examples 11-17 (or any other example described herein), wherein the fluid sample comprises at least one of a bodily fluid, a water sample, a beverage, a cleaning fluid, or a solvent.

Example 19 includes the subject matter of any of examples 11-18 (or any other example described herein), wherein the module comprises: an actuator to activate in association with the application of the fluid sample to probe the non-planar structure; and a sensor to obtain a measurement associated with the non-planar structure responsive to an activation of the actuator.

Example 20 includes the subject matter of any of examples 11-19 (or any other example described herein), wherein the substrate comprises a semiconductor substrate and at least a portion of the module comprises active circuitry located below a surface of the semiconductor substrate, and wherein the non-planar structure is at least partially formed in an opening on the surface of the semiconductor substrate.

Example 21 is a method, comprising: probing a bead to identify a characteristic of the bead after an osmotic response of the bead to a fluid sample; obtaining a measurement of the bead responsive to the probing; and calculating a value indicative of a characteristic of the fluid sample based on the measurement of the bead.

Example 22 includes the subject matter of example 21 (or any other example described herein), wherein the characteristic of the bead comprises volume, and the method further comprises at least one of: identifying a change of capacitance corresponding to movement of a plate of a capacitor responsive to a volumetric change of the bead associated with the osmotic response; identifying a change of light received on an optical sensor corresponding to movement of the plate of the capacitor responsive to the volumetric change of the bead associated with the osmotic response; identifying a change of capacitance corresponding to an expansion of a dielectric gap responsive to the volumetric change of the bead associated with the osmotic response; identifying a change of an inductance corresponding to the movement of a coil of an inductor responsive to the volumetric change of the bead associated with the osmotic response; or identifying an electric coupling of a circuit corresponding to movement of a conductive portion of a shell of the bead responsive to the volumetric change of the bead associated with the osmotic response.

Example 23 includes the subject matter of any of examples 21-22 (or any other example described herein), wherein the characteristic of the bead comprises surface tension, and the method further comprises: applying a force to a portion of a shell of the bead; and identifying at least one of deformation of the bead, a force imparted by the bead on a reference object, or a movement of the bead relative to the reference object.

Example 24 includes the subject matter of any of examples 21-23 (or any other example described herein), wherein the characteristic of the bead comprises vibrational response, and the method further comprises: applying a vibrational force to a portion of the bead; and identifying a movement of a different portion of the bead.

Example 25 includes the subject matter of any of examples 21-24 (or any other example described herein), wherein the characteristic of the bead comprises an electrical characteristic, and the method further comprises: applying current to a circuit comprising the bead; and identifying an electrical characteristic of a node of the circuit.

Example 26 includes the subject matter of any of examples 21-25 (or any other example described herein), further comprising: illuminating the bead with a UV (ultra violet) spectrum light source after the osmotic response of the bead to the fluid sample; and identifying a spectrum responsive to illuminating the bead.

Example 27 includes the subject matter of any of examples 21-26 (or any other example described herein), wherein the characteristic of the bead comprises a mass of the bead, and wherein obtaining the measurement of the bead comprises reading a load sensor corresponding to the bead.

Example 28 includes the subject matter of any of examples 21-27 (or any other example described herein), further comprising: identifying a percentage of the fluid sample that is not absorbed by the bead; and utilizing the percentage to identify the measurement of the bead.

Example 29 includes the subject matter of any of examples 21-28 (or any other example described herein), wherein the characteristic of the bead comprises surface area, and wherein the obtaining the measurement of the bead comprises sensing a plurality of pads to identify which pads of the plurality of pads is in contact with the bead.

Example 30 includes the subject matter of any of examples 21-29 (or any other example described herein), wherein the fluid sample comprises at least one of a bodily fluid, a water sample, a beverage, a cleaning fluid, or a solvent.

Example 31 is a method, comprising: forming an opening in a substrate; depositing a bead in the opening, the bead having a selectively permeable curved exterior and a core defined by the selectively permeable curved exterior, wherein a content of the core are to change by osmosis responsive to application of a fluid sample to the bead; and forming a fluid channel on the substrate, the fluid channel to couple the opening to a fluid reservoir.

Example 32 includes the subject matter of example 31 (or any other example described herein), further comprising forming a sensor on the substrate to obtain a measurement of the bead.

Example 33 includes the subject matter of any of examples 31-32 (or any other example described herein), further comprising forming a sensor on the substrate to obtain a measurement of a fluid content of the fluid reservoir.

Example 34 includes the subject matter of any of examples 31-33 (or any other example described herein), further comprising forming a sensor on the substrate to identify whether the fluid reservoir is empty.

Example 35 includes the subject matter of any of examples 31-34 (or any other example described herein), wherein a portion of the selectively permeable curved exterior of the deposited bead protrudes from the opening.

Example 36 is an electrical system, comprising: an actuator to stimulate a bead to identify a characteristic of the bead after an osmotic response of the bead to a fluid sample; a sensor to obtain a measurement of the bead responsive to activation of the actuator; and a processor to calculate a value indicative of a characteristic of the fluid sample based on the measurement of the bead.

Example 37 includes the subject matter of example 36 (or any other example described herein), wherein the actuator comprises an optical component.

Example 38 includes the subject matter of any of examples 36-37 (or any other example described herein), wherein at least one of the actuator or the sensor comprises a piezoelectric component.

Example 39 includes the subject matter of any of examples 36-38 (or any other example described herein), wherein the actuator comprises a circuit.

Example 40 includes the subject matter of any of examples 36-39 (or any other example described herein), further comprising a display to output the value.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims.

Where the disclosure recites "a" or "a first" element or the equivalent thereof, such disclosure includes one or more such elements, neither requiring nor excluding two or more such elements. Further, ordinal indicators (e.g., first, second or third) for identified elements are used to distinguish between the elements, and do not indicate or imply a required or limited number of such elements, nor do they indicate a particular position or order of such elements unless otherwise specifically stated.

What is claimed is:

1. An apparatus, comprising:
a substrate;
a non-planar structure formed on the substrate, the non-planar structure having a semi-permeable membrane and a core defined by the semi-permeable membrane, the semi-permeable membrane to permeate a substance to or from the core, wherein a characteristic of the non-planar structure is to change responsive to the permeation of the substance through the semi-permeable membrane; and
a sensor formed on the substrate, the sensor to obtain a measurement in response to exposure of the non-planar structure to a fluid sample; and
circuitry to identify a value indicative of a characteristic of the fluid sample based on the measurement.

2. The apparatus of claim 1, further comprising an actuator to perform at least one of apply current to the non-planar structure to obtain the measurement using the sensor, project light on the non-planar structure to obtain the measurement using the sensor, apply mechanical stress to an exterior surface of the semi-permeable membrane to obtain the measurement using the sensor, or apply an air pressure change to the exterior surface of the semi-permeable membrane to obtain the measurement using the sensor.

3. The apparatus of claim 2, wherein the actuator comprises at least one of a visible spectrum light source, a UV (ultra violet) spectrum light source, or an infrared spectrum light source.

4. The apparatus of claim 2, wherein the light comprises a laser beam.

5. The apparatus of claim 1, wherein the sensor is to measure a volume of a reservoir fluidly coupled to the non-planar structure responsive to the permeation of the substance through the semi-permeable membrane.

6. The apparatus of claim 1, wherein the non-planar structure is formed in an opening on a surface of the substrate.

7. The apparatus of claim 1, wherein the semi-permeable membrane is to protrude from a surface of the substrate.

8. The apparatus of claim 1, wherein the non-planar structure is formed entirely within an opening on a surface of the substrate.

9. The apparatus of claim 1, wherein the non-planar structure is to expand or contract responsive to absorption or perspiration of the fluid sample.

10. The apparatus of claim 1, wherein a shape of the non-planar structure comprises at least one of a sphere, a spheroid, a hemisphere, a truncated sphere, or a truncated spheroid.

11. An apparatus, comprising:
a substrate;
a non-planar structure formed on the substrate, the non-planar structure having a curved exterior and a core defined by the curved exterior, wherein a content of the core is to change by osmosis responsive to application of a fluid sample to the non-planar structure; and
a module formed on the substrate to identify a change of a characteristic of the non-planar structure responsive to the application of the fluid sample to the non-planar structure, the identified change indicative of a property of the fluid sample.

12. The apparatus of claim 11, wherein the module comprises a processor to:
identify a measurement of a change in at least one of capacitance, resistance, or inductance responsive to a volumetric change of the non-planar structure; and
calculate a value indicative of the property of the fluid sample based on the measurement.

13. The apparatus of claim 11, wherein the module comprises a processor to:
identify a measurement of a change of position of a portion of the curved exterior responsive to a force applied to a different portion of the curved exterior; and
calculate a value indicative of the property of the fluid sample based on the measurement.

14. The apparatus of claim 11, wherein the module comprises a processor to:
identify a measurement of a change of vibrational response of the non-planar structure responsive to a force applied to the non-planar structure; and
calculate a value indicative of the property of the fluid sample based on the measurement.

15. The apparatus of claim 11, wherein the module comprises a processor to:
identify a measurement of a change in capacitance of a circuit that includes the non-planar structure; and
calculate a value indicative of the property of the fluid sample based on the measurement.

16. The apparatus of claim 11, wherein the module comprises a processor to:
identify a measurement of a change of an electrical characteristic of a circuit responsive to a change in conductivity of the non-planar structure; and
calculate a value indicative of the property of the fluid sample based on the measurement.

17. The apparatus of claim 11, wherein the module comprises a processor to:
identify a measurement of a change of at least one of optical transparency, optical reflection, or optical absorption of the non-planar structure; and calculate a value indicative of the property of the fluid sample based on the measurement.

18. The apparatus of claim 12, wherein the fluid sample comprises at least one of a bodily fluid, a water sample, a beverage, a cleaning fluid, or a solvent.

19. The apparatus of claim 11, wherein the module comprises:
   an actuator to activate in association with the application of the fluid sample to probe the non-planar structure; and
   a sensor to obtain a measurement associated with the non-planar structure responsive to an activation of the actuator.

20. The apparatus of claim 11, wherein the substrate comprises a semiconductor substrate and at least a portion of the module comprises active circuitry located below a surface of the semiconductor substrate, and wherein the non-planar structure is at least partially formed in an opening on the surface of the semiconductor substrate.

21. A method, comprising:
   probing a bead to identify a characteristic of the bead after an osmotic response of the bead to a fluid sample;
   obtaining a measurement of the bead responsive to the probing; and
   calculating a value indicative of a characteristic of the fluid sample based on the measurement of the bead.

22. The method of claim 21, wherein the characteristic of the bead comprises volume, and the method further comprises at least one of:
   identifying a change of capacitance corresponding to movement of a plate of a capacitor responsive to a volumetric change of the bead associated with the osmotic response;
   identifying a change of light received on an optical sensor corresponding to movement of the plate of the capacitor responsive to the volumetric change of the bead associated with the osmotic response;
   identifying a change of capacitance corresponding to an expansion of a dielectric gap responsive to the volumetric change of the bead associated with the osmotic response;
   identifying a change of an inductance corresponding to the movement of a coil of an inductor responsive to the volumetric change of the bead associated with the osmotic response; or
   identifying an electric coupling of a circuit corresponding to movement of a conductive portion of a shell of the bead responsive to the volumetric change of the bead associated with the osmotic response.

23. The method of claim 21, further comprising:
   identifying a percentage of the fluid sample that is not absorbed by the bead; and
   utilizing the percentage to identify the measurement of the bead.

24. The method of claim 21, wherein the characteristic of the bead comprises surface area, and wherein the obtaining the measurement of the bead comprises sensing a plurality of pads to identify which pad of the plurality of pads is in contact with the bead.

25. The method of claim 21, wherein the fluid sample comprises at least one of a bodily fluid, a water sample, a beverage, a cleaning fluid, or a solvent.

* * * * *